United States Patent [19]
Lai et al.

[11] Patent Number: 5,384,136
[45] Date of Patent: * Jan. 24, 1995

[54] PSYLLIUM-ENRICHED DOUGH PRODUCTS AND METHOD FOR MAKING THE SAME

[75] Inventors: Grace H. Lai, Portage, Mich.; Richard D. Wullschleger, Blandon, Pa.

[73] Assignee: Kellogg Company, Battle Creek, Mich.

[ * ] Notice: The portion of the term of this patent subsequent to Jan. 17, 2012 has been disclaimed.

[21] Appl. No.: 123,353

[22] Filed: Sep. 17, 1993

[51] Int. Cl.⁶ .................. A21D 8/02; A23L 1/0526
[52] U.S. Cl. ........................... 426/19; 426/21; 426/551; 426/573
[58] Field of Search .............. 426/549, 573, 551, 19, 426/21

[56] References Cited

U.S. PATENT DOCUMENTS

| | | | |
|---|---|---|---|
| 3,148,114 | 9/1964 | Fahrenback et al. | 167/55 |
| 3,574,634 | 3/1971 | Singer | 99/83 |
| 3,836,680 | 9/1974 | Salza | 426/557 |
| 3,843,818 | 10/1974 | Wren et al. | 426/557 |
| 3,992,554 | 11/1976 | Blake et al. | 426/557 |
| 4,348,379 | 9/1982 | Kowalsky et al. | 424/34 |
| 4,766,004 | 8/1988 | Moskowitz | 426/658 |
| 4,849,222 | 7/1989 | Broaddus | 424/195 |
| 4,950,140 | 8/1990 | Pflaumer et al. | 424/439 |
| 5,015,486 | 5/1991 | Franssell et al. | 426/243 |
| 5,024,996 | 6/1991 | Ringe | 514/54 |
| 5,026,689 | 6/1991 | Ringe et al. | 514/57 |
| 5,095,008 | 3/1992 | Pflaumer et al. | 514/23 |
| 5,101,717 | 4/1992 | Manser et al. | 99/474 |
| 5,122,378 | 6/1992 | Hauser et al. | 426/242 |
| 5,139,806 | 8/1992 | Hauser et al. | 426/496 |
| 5,223,298 | 6/1993 | Wullschleger et al. | 426/549 |
| 5,227,248 | 7/1993 | Wullschleger et al. | 426/549 |

*Primary Examiner*—Donald E. Czaja
*Assistant Examiner*—Mary S. Mims
*Attorney, Agent, or Firm*—Felfe & Lynch

[57] ABSTRACT

The invention provides for a dough product, that is enriched with a psyllium composition. The psyllium may range from about 1.0 to about 5.0 grams per one ounce. The dough product can include an amount of gluten to increase its volume. Also provided is a method for making the dough products. These dough products are useful in lowering serum cholesterol levels as well as for increasing dietary fiber in the diet of the individual consuming them.

14 Claims, No Drawings

PSYLLIUM-ENRICHED DOUGH PRODUCTS AND METHOD FOR MAKING THE SAME

FIELD OF THE INVENTION

This invention relates to psyllium-enriched dough products. The dough products may be administered to humans and animals susceptible to or afflicted with hypercholesterolemia to lower serum cholesterol or to individuals in need of dietary regulation. The invention also relates to a method for producing the dough products, in which psyllium is subjected to pretreatment, i.e., pre-wetting.

BACKGROUND OF THE INVENTION

Psyllium is a known mucilaginous material which has found extensive use in bulk laxatives. The source of psyllium is the seeds of plants of the Plantago genus, which grow in certain sub-tropical regions. Since it is believed by those skilled in the art that the active ingredient of psyllium is the psyllium seed gum, which is located primarily in the seed husk, present technology uses the ground seed husk as the source of psyllium. However the whole seed is also known as a psyllium source, as well as the dehusked psyllium seed.

It is well known that psyllium decreases plasma triglycerides and LDL cholesterol, particularly in humans. The specific use of a psyllium hydrophilic muciloid to lower cholesterol in serum was documented by Anderson et al., Arch. Intern. Med. Vol. 148, February 1988, 292–296 (1988), Anderson et al., Am J. Clin Nutr. Vol.56, p. 93–98, (July 1992). It has been theorized that psyllium, which belongs to a class of gel forming soluble fibers, disrupts the absorption or metabolism of cholesterol by binding, entrapping, absorbing, or otherwise interfering with the reabsorption of bile acids across the intestinal lumen. It is also theorized that the soluble fiber interferes with the intraluminal formation of micelies, resulting in decreased cholesterol and bile acid reabsorption. The end result is that more bile acids and dietary cholesterol are ultimately excreted in the feces, resulting in a decreased level of serum cholesterol.

However, due to its mucilaginous nature, psyllium acquires a slimy or adhesive texture and mouthfeel upon hydration. Psyllium normally forms a gelatinous mass when contacted with water and exhibits poor dispersibility and mixability in water. Psyllium also develops a distinctive, undesirable flavor in the presence of heat and moisture which further limits its use in food products. This slimy mouthfeel is unpalatable and, accordingly, various additives have been incorporated in psyllium-containing ingestible compositions in order to mask the undesirable texture and mouthfeel of the psyllium.

Notwithstanding the undesirable flavor and texture imparted to an ingestible composition by psyllium or psyllium husks, various psyllium-containing foodstuffs have been proposed which purport to take advantage of the natural digestion regulation properties of psyllium, or the satiating or "fullness-feeling" effect of psyllium. See, for example, U.S. Pat. Nos. 3,574,634 and 4,348,379.

In addition, it has been suggested, for example, in U.S. Pat. No. 3,148,114, the whole psyllium husks, such as the ground husks of the seed of Plantago psyllium, lower blood cholesterol upon oral administration thereof. Further, it has also long been known to use small quantities of psyllium, such as less than 1%, as a thickener in foodstuffs, such as in ice cream, puddings and the like.

Finally, U.S. Pat. No. 4,849,222 discloses a medicament composition for reducing blood cholesterol levels in humans and lower animals which comprises a mixture of psyllium seed gum, or source of psyllium seed gum, and a nonabsorbable, nondigestible polyol polyester.

However, as set forth above, the mucilaginous nature of psyllium husks presents grave processing difficulties, and prior attempts to produce a palatable, ready-to-eat food product containing psyllium have not resulted in a satisfactory product to date, particularly, with respect to flavor and texture or mouthfeel.

Attempts have been made to incorporate psyllium into foodstuffs, so that the fiber can be consumed as part of a regular meal or other aspect of a normal diet, without any connotation or association with medicines, as well as with acceptable organoleptic properties. Examples of the patent literature involving psyllium incorporated into foodstuffs are U.S. Ser. Nos. 817,244 and 819,569 both filed Jan. 6, 1992, now U.S Pat. Nos. 5,223,298 and 5,227,248, both of which are incorporated by reference. These patents teach psyllium containing ready to eat cereals. Additional examples of cereals containing psyllium are set forth by Moskowitz, U.S. Pat. No. 4,766,004; Ringe U.S. Pat. No. 5,024,996; and Ringe et al., U.S. Pat. No. 5,026,689. Other foodstuffs which include psyllium are taught in U.S. Pat. Nos. 5,095,008 and 5,950,140 both of which teach cookies with incorporated psyllium, U.S. Pat. No. 5,015,486, which teaches microwaveable muffins, and U.S. Pat. No. 5,024,996 in which teaches almond paste containing compositions, such as marzipan. U.S. Pat. No. 5,164,216 describes bread suitable for microwaving which contain required levels of shortening and fiber. Psyllium muciloid is mentioned as a potentially useful fiber source; however, no examples of its use are given, nor is there any discussion of problems associated therewith.

In fact, psyllium cannot be routinely incorporated into dough products such as bread. It has been found that "neat" psyllium, when combined with other ingredients, leads to an unpalatable product. The invention described herein, however, teaches a product which overcomes the problems experienced when psyllium is directly incorporated into dough products. It has been found, surprisingly, that the simple step of prewetting psyllium prior to incorporating it into a bread product eliminates the organoleptic objections encountered with non-prewetted psyllium.

It is therefore a principal object of this invention to provide for an effective and economically produced food composition comprising psyllium in a dough product for use in bread or bakery products. A method for the production of the psyllium dough product is also provided herein.

It is a further object of this invention to provide for a bread or bakery composition containing psyllium which is palatable and suitable for human consumption in a food product while providing the benefits of lowered serum cholesterol levels.

SUMMARY OF THE INVENTION

This invention provides for a dough product, i.e., bread or baked food product, enriched with pretreated psyllium, in such a way so as to render the psyllium soluble and palatable in the food product. The pretreatment of psyllium prior to mixing the other bread ingredients provides for a palatable psyllium enriched dough for the manufacture of bread and other baked goods. The invention also provides for a psyllium enriched dough product which also contains an amount of gluten, e.g. vital wheat gluten, which is added during the processing of the psyllium-enriched dough product of this invention and which is responsible for the increase in volume in the final product.

DETAILED DESCRIPTION OF THE INVENTION

It is has been found that pretreating psyllium with water prior to incorporation of other ingredients results in a dough product with satisfactory mouthfeel, texture, and taste. When the psyllium is added directly with other ingredients, the psyllium absorbs the water instantly and prevents gluten development. When the grain, e.g. wheat, is ground and mixed with water, the grain protein forms a complex, semisolid structure called gluten which is both plastic and elastic. Gluten formation and development is important during the baking processes because the gluten expands to accommodate the gases produced by the yeast.

Therefore, before the incorporation of psyllium to the main bread ingredient, e.g., wheat, rye, flour, the psyllium must be pretreated in order to ensure adequate absorption and successful incorporation into the dough product.

The psyllium product may be incorporated in the form of 98% purity extruded psyllium or in the form of cold extruded psyllium containing pellets. According to the cold extrusion process, the psyllium is mixed with flour, sugar and Myvaplex and extruded to form a "cold form" pellet by the cold extrusion process. The pellets are dried and ground for use as psyllium raw material. The ground psyllium manufactured from the cold formed pellets is subjected to a pretreatment process which involves prewetting psyllium with water. By this cold extrusion step, the hydration rate of the psyllium is retarded and allows for the smooth incorporation into the dough product.

This invention will be better understood by reference to the following controls and examples, which are included here for purposes of exemplification and are not to be construed as limitations.

CONTROL 1

This control experiment demonstrates that without a pretreatment step, psyllium cannot be successfully incorporated into a dough product. A sample of 98% purity extruded psyllium, as described below, was used in a bread recipe, as indicated:

|  | Amount | % (Dry Basis) |
|---|---|---|
| Bread Flour | 350.00 g | 68.36 |
| Sugar | 25.00 g | 5.48 |
| Dry Milk | 9.00 g | 1.83 |
| Shortening | 21.00 g | 4.60 |
| Water | 295.00 g | 0.00 |
| Psyllium (extruded 98% purity) | 82.00 g | 16.51 |
| Yeast | 6.70 g | 1.47 |

A 98% purity extruded psyllium product can be used as the starting material. The 98% purity extruded psyllium can be prepared utilizing the following parameters. The psyllium is extruded through a WP/twin screw extruder at a minimum temperature of 240° F. The moisture of the material in the extruder is maintained at approximately 15.5% to about 17.5% water during the extrusion process. The approximate feed rate for the psyllium product is about 15 to 17 kg per minute, preferably at about 16 kg per minute. The finished 98% purity extruded psyllium product has a moisture content of about 6–10%.

The ingredients were combined in an automatic bread baking machine, and manufacturer's instructions were used. The bread product contained approximately 3.4 gms of psyllium per one ounce serving.

The psyllium used in this example was not subjected to cold extrusion or to the prehydration, e.g., prewetting step.

The resulting dough had a very strong psyllium odor during baking. The mixed dough was also very dry and did not remain intact. There was additionally no increase in volume during the rising step. The crumbs were very dense and the crust was very dark, e.g., a brown to black color. The failures in the product were such that it was not subjected to taste testing.

CONTROL 2

Following control 1, another attempt was made to make a psyllium enriched bread with a smaller amount of psyllium, e.g., 3.4 gms of psyllium per two ounce serving (i.e., 1.7 g per slice). Cold extruded psyllium pellets (50%) as described below and in U.S. Ser. Nos. 08/123,342, 08/123,352, filed Sep. 17, 1993, were ground to pass a 1.0 mm screen.

The following ingredients were combined to form 50% cold extrusion pellets:

| 55.6 lbs | rice flour |
|---|---|
| 48.0 lbs | sucrose |
| 109.9 lbs | psyllium 98% purity |
| 2.0 lbs | Myvaplex |

The cold extrusion process takes place by extruding the above ingredients through a WP twin screw extruder to form the pellets. A cool water bath is applied to the extruder so as to maintain the temperature during the extrusion process. The extruder preferably contains a means to measure the temperature during the extrusion at two zones. Zone 1 is the point at which the mixture is fed through the extruder. Zone 2 is where the mixture is substantially mixed and extruded. During cold extrusion, the temperatures maintained in zone 1 is approximately 60° to 80° F., preferably the temperature is about 73° F. The temperatures in zone 2 is kept at approximately 160° to 180° F., preferably the temperature in zone 2 is about 169° F. The pellets are then extruded through a die and dried for about 50 to 90 minutes, preferably 70 minutes, at about 150° F. to a maximum of 200° F., to a moisture content of approximately 6–10%, preferably about 8%.

After the pellets were formed, they were ground to prepare the psyllium flour. The psyllium of this example, was not subjected to prewetting. The psyllium was used in its dry, ground form. The recipe for this bread is as follows:

|  | Weight (g) | Dry Basis % |
|---|---|---|
| Bread flour | 290.80 | 56.58 |
| Sugar | 30.28 | 6.61 |
| Dry Milk | 10.94 | 2.21 |

| -continued | Weight (g) | Dry Basis % |
|---|---|---|
| Salt | 6.03 | 1.32 |
| Shortening | 21.94 | 4.79 |
| Water | 334.16 | 0.00 |
| Vital gluten flour | 48.21 | 6.79 |
| Yeast | 6.80 | 4.19 |
| Psyllium (as above) | 90.02 | 12.22 |

Analysis of the product showed that the 50% cold extruded psyllium did not swell as much as the 98% purity extruded psyllium, i.e., the swell volume for the cold extruded psyllium was approximately one half the swell volume for the extruded psyllium. The resulting dough was very dry. In fact, the original recipe called for 309 g of water, but 25g additional water was necessary in order to produce a reasonable dough. The finished loaf had very dense crumbs, with a dark colored crust. The loaf volume was also very small, and similar to that produced in the first control. This bread sample was not palatable to the taste testing team.

EXAMPLE 1

The following example illustrates the efficacy of pretreating the psyllium with water prior to adding the psyllium to the other ingredients of the dough composition. This psyllium dough product contained the following ingredients:

| Ingredient | Amount (g) | % Dry Basis |
|---|---|---|
| Bread flour | 350.0 | 67.98 |
| Sugar | 30.0 | 6.54 |
| Dry Milk | 12.0 | 2.42 |
| Salt | 3.0 | 0.65 |
| Shortening | 21.0 | 4.58 |
| Water | 237.0 | 0.00 |
| Yeast | 6.7 | 1.40 |
| Psyllium (extruded 98% purity) | 82.0 | 16.42 |
| Water | 60.0 | 0.00 |

The amount of psyllium added was such that a one ounce portion of the resulting bread would contain 3.4 g of psyllium.

The psyllium was first prewet with 60 g of water. The other ingredients were mixed before adding the prewetted psyllium to the dough. The first dough consisted of the dough ingredients with the exception of the prewetted psyllium and the yeast. After the dough was kneaded for twenty minutes, the prewetted psyllium and the yeast were added to the dough and further kneaded.

Water was sprayed into the psyllium gradually while the psyllium was mixed, in order to prevent any lumping from occurring. The psyllium particles were kept small in order to maximize incorporation in the dough.

The amount of sugar was increased in this example as compared to Controls 1 and 2 to provide more material for the yeast to act upon. The amount of salt was decreased in this example, to produce a low salt bread product. The same baking protocol as was used in Controls 1 and 2 was followed.

The resulting loaf was small, e.g., approximately one half the size of the standard loaf. The crumb was very dense with very small air cells. However, there is no detectable psyllium odor while the bread is baked and during consumption.

EXAMPLE 2

The following example further illustrates that the psyllium had to be prewetted before addition to the dough in order to achieve acceptable incorporation. The following ingredients were incorporated into a dough composition:

| Ingredient | Amount (g) | % Dry Basis |
|---|---|---|
| Bread flour | 380.0 | 75.27 |
| Sugar | 30.0 | 6.67 |
| Dry Milk | 11.0 | 2.27 |
| Salt | 6.0 | 1.33 |
| Butter (Margarine) | 21.0 | 4.67 |
| Water | 249.0 | 0.00 |
| Yeast | 6.7 | 1.43 |
| Psyllium (extruded 98%) | 41.0 | 8.37 |
| Water | 30.0 | 0.00 |

This dough was prepared in a manner similar to example 3. However, the psyllium percentage, by dry weight, was decreased by 50% so as to yield a product containing 1.7 of psyllium per ounce. The prewetted psyllium was added to the dough with the yeast after the first twenty minutes of kneading.

The finished dough product did not rise as much as the standard loaf, although this loaf had a larger volume than that produced in example 1. The crumb was dense but there was no detectable psyllium odor. The bread was aromatic during the baking process. The bread also had good sensory evaluation and was considered palatable by a tasting team.

EXAMPLE 3

The following examples illustrate a further embodiment according to this invention. The foregoing examples provide for a psyllium dough product which when baked does not rise to the volume of a standard size loaf. The following ingredients were combined according to the process detailed below to prepare a bread product which rises to a standard size loaf.

| Ingredient | Amount (g) | % Dry Basis |
|---|---|---|
| Bread flour | 292.68 | 57.23 |
| Whole wheat flour | 50.53 | 44.63 |
| Sugar | 30.19 | 6.63 |
| Dry Milk | 11.16 | 2.27 |
| Salt | 5.94 | 1.30 |
| Shortening | 20.42 | 4.48 |
| Water | 249.0 | 0.00 |
| Vital gluten flour | 38.80 | 7.94 |
| Yeast | 6.71 | 1.41 |
| Psyllium (extruded 98%) | 44.41 | 8.95 |
| Water | 50.98 | 0.00 |

As with example 2, the bread product contained 1.7 g of psyllium per ounce.

In order to prepare a dough product which rises to the standard size loaf, a smaller amount of bread flour was used and was replaced with whole wheat flour (graham flour), and vital gluten. The dry ingredients listed above were mixed in a pan and water was added to knead the dough. The prewetted psyllium was processed, as in example 1. Baking was carried out as on the prior examples.

The height of the finished loaf was 4.5 inches in the center and 3.5 inches at the edge. There was a nice crumb texture and cell structure. The loaf had dense crumb structure. The finished product was slightly wet;

however, the aroma and texture were deemed acceptable by a tasting team, especially after toasting. No objectionable psyllium taste was detected.

EXAMPLE 4

The following further illustrates the necessity of pretreating the psyllium. The psyllium used in this example is the cold extruded psyllium pellets, ground to prepare the raw material. The following ingredients were combined to prepare the dough product:

| Ingredient | Amount (g) | % Dry Basis |
|---|---|---|
| Bread flour | 289.28 | 56.77 |
| Sugar | 30.23 | 6.66 |
| Dry Milk | 11.53 | 2.35 |
| Salt | 6.19 | 1.36 |
| Shortening | 20.97 | 4.62 |
| Water | 259.49 | 0.00 |
| Vital gluten flour | 44.86 | 9.21 |
| Yeast | 6.80 | 1.43 |
| Psyllium (cold extruded 50%) | 90.99 | 17.59 |
| Water | 48.21 | 0.00 |

The example used a cold extruded psyllium (50%) pellet product for the dough composition. The cold extruded psyllium product was prepared according to Control 2 as set forth above and also described in Ser. Nos. 08/123,342, 08/123,352, filed Sep. 17, 1993. The psyllium pellets were ground into a powder. The psyllium powder was then prewetted before adding to the remaining ingredients.

This dough product was baked in the automatic bread baker of example 1, as described supra, but rapid bake mode was used, which is approximately one hour and thirty minutes faster than the earlier bake trials. The resting time between the first and second steps was reduced to only 5 minutes rather then the usual thirty minutes. The yeast was mixed with other dry ingredients rather than introducing it during the resting time. Psyllium (prewet) was added during the rest phase.

The finished dough product had a golden crust. The loaf had very good cell structure and good aroma. The loaf height at the center was five inches and 4.5 inches at the edge. The crumb was damp, probably due to excess water retention by psyllium. It was found that the addition of yeast earlier in the dough processing improves the loaf volume. The bread was deemed the best of all loaves tested.

EXAMPLE 5

The cholesterol lowering effect of the psyllium enriched dough of this invention on certain individuals is confirmed by the following study.

Over the course of six months, a long term intervention study is conducted to test the effect of the psyllium enriched product on the level of serum cholesterol on sample size of 250 hypercholesterolemic individuals. Individuals chosen for this study are at risk for mild abnormalities in their cholesterol levels. Generally, the study targets individuals with plasma LDL-cholesterol levels at 130 to 220 mg/dl, with the proviso that their triglycerides levels are less than 300 mg/dl. There is an initial eight week dietary instruction and stabilization period where lipid criteria are ascertained.

According to the protocol of the intervention study, the individuals participating in the study are divided into four groups. The groups are administered varying number of servings of a psyllium enriched food product to determine whether there is a dose dependent hypocholesterolemic effect. The participants are given a choice of psyllium enriched food products: R-T-E-cereal, bread, snack bars, and pasta, which are packaged in zero and 3 mg psyllium servings.

Group A is given three servings of the placebo product per day and is not administered a psyllium food product at all.

Group B is given two servings of the test product and one serving of the placebo product per day.

Group C is given one serving of the test product and two servings of the placebo product per day.

Group D is given three servings of the test product per dayu.

The serum cholesterol levels are tested periodically during the study by taking blood samples and determining cholesterol level in the serum.

The cholesterol levels decrease from baseline over the course of the study indicating the hypocholesterolemic effect of psyllium enriched products. The study further shows that the decrease in serum cholesterol is in proportion to the dosage units of psyllium product ingested.

EXAMPLE 6

A study was also conducted to test the efficacy of psyllium enriched products in reversing the rise in plasma total cholesterol in hamsters fed a diet with added cholesterol.

The hamsters were administered a diet consisting of 20% protein, 14% fat, 15% sugar, 1% NaCl. The amount of total dietary fiber was targeted at 10%, which includes non-soluble and soluble fiber.

The control group was given a food product without (Product A) and with added cholesterol (Product B). The control product with added cholesterol (Product B) and the psyllium bread test product (Product C) contained about 0.125% cholesterol.

The control products without and with cholesterol (Products A and B) and the psyllium enriched bread product (Product C) contained the following ingredients as a percentage of the entire composition:

| | A | B | C |
|---|---|---|---|
| 1. vitamin/mineral amino acid mixture | 7.95% | 7.95% | 7.95% |
| 2. Test Material | — | — | 39.1 |
| 3. wheat bran | 24.0 | 24.0 | 10.4 |
| 4. Casein | 18.0 | 18.0 | 12.0 |
| 5. Safflower Oil | 4.0 | 4.0 | 3.0 |
| 6. Sucrose | 14.3 | 14.3 | 9.7 |
| 7. NaCl | 0.99 | 0.99 | 0.37 |
| 8. Starch | 23.8 | 23.6 | 10.4 |
| 9. Cholesterol | — | 0.125 | 0.125 |
| 10. Beef Tallow | 7.0 | 7.0 | 7.0 |

It was found that the total cholesterol level for hamsters fed with Product A containing no added cholesterol, measured in mg/dl, was 157.0±31.0. It was also found that the total serum cholesterol levels of hamsters fed Product B with added cholesterol, and of hamsters fed on hamsters fed psyllium enriched bread Product C, decreased from 221.7±27.7 to 149.1±21.5. This study establishes that a psyllium enriched bread product fed to hamsters on an elevated cholesterol diet reduces the level of total cholesterol.

The psyllium bread product now having an established hypocholesterolemic effect on an elevated cholesterol diet was then administered to individuals for a taste preference test comparing conventional and psyllium enriched bread.

EXAMPLE 7

The following test was carried out to determine the overall preference for standard white bread and bread with psyllium.

The control white, low fiber bread and psyllium enriched bread was produced according to Applicants' specifications.

Sixty-two panelists were given half a slice of each of the control bread and the test bread both toasted and spread with strawberry jam. The serving size was half a slice of bread. The bread was toasted and spread with one teaspoon of strawberry jam prior to slicing. The illumination was white.

The panelists were asked to determine which bread they preferred. Thirty-one of the sixty-two panelists preferred the test bread with psyllium, p-value=0.500. A significance criteria of p=0.05 was set prior to this test. Based on this test, no preference was found between the standard white low fiber bread and the test bread made with psyllium when served with strawberry jam.

These foregoing examples show that the dough products may be made with prewetted, extruded psyllium. Where the psyllium is subjected to pretreatment with water, the dough is easily handled and the finished product has good aroma and taste. There is little detectable psyllium odor. The examples also show that where psyllium is pretreated according to the processes delineated, the mucilaginous fiber is rendered soluble and dispersable in water.

The examples demonstrate that prewetted psyllium is required to produce an acceptable bread or bakery product. It is especially preferred that the prewetted psyllium be cold extruded psyllium.

The examples all use various ingredients besides yeast, flour and water, which are the minimum ingredients required to make a yeast leavened bread product. It will be understood, e.g., that ingredients such as salt, dry milk powder, sweeteners, shortening, etcetera, are options which, while they may lead to a better product, are not required. In the case of shortening, for example, cholesterol free options, such as margarine or vegetable oil may be used, as can butter. Sugar, honey, molasses, corn syrup etcetera, are examples of sweeteners which may be used. Even in the case of leavening agents, while yeast is by far the most common and preferred leaven, the art is familiar with, e.g., "sourdough" leavens (Lactobacillus), and other leavening agents. More than one leaven may be added as well, such as bicarbonates.

The key ingredient of this invention is the prewetted psyllium. Prewetted psyllium, as will be seen, requires a pretreatment step, i.e., mixing with water. The psyllium so treated may be any form thereof, such as cold, extruded psyllium which has been ground to a powder, extruded psyllium, and so forth. Prewetted psyllium is generally prepared by adding water to the psyllium and allowing the mixture to temper before combining with other ingredients. It is preferred to combine the water and psyllium in a range of from about 0.75:1 to 1.25:1 (by weight). A ratio of 1:1 is particularly preferred.

The tempering period for the prewetted psyllium may vary. The key aspect is that the prewetted psyllium possesses a free flowing nature as compared to the non-prewetted material. The prewetting step must be performed shortly before use because the high water level affects its stability. If the prewetted material is allowed to temper for more than about 24–48 hours, this property is lost. Moreover, an extensive time period may encourage the growth of microorganisms. Therefore, the prewetted psyllium should not be permitted to temper for more than about 24–48 hours. It is especially preferred to allow it to temper overnight (10–12 hours) or even less. It is especially preferred to use the psyllium at no more than about 30 minutes after prewetting treatment.

In some of the examples, vital gluten was added to improve load size of the resulting product. This is a standard additive in commercial leavened bread products, but should not be seen as a requirement of the final product.

A flour component is required in the bread product. Most usually, this will be a wheat flour, such as "bread flour", or white flour. So-called "graham" or whole-wheat flour may be used as well. All mills of these flours are possible in the invention, as are non-wheat flours, such as rye, corn, oat, hybrids such as triticale, and so forth. These flours may be used alone or in combination. When no wheat based flour is used, it may be desirable to incorporate vital gluten or gluten in some form so as to give the baked product strength, stability, and height.

Additional ingredients may be added to the bread products of the invention. Some of these are set forth supra. Others include eggs or egg components, whole milk or fractions of milk, vegetable or fruit ingredients (e.g., carrot, pumpkin, banana, zucchini), whole grains, seeds, flavor extracts, preservatives, and so forth.

The terms "dough product" and "baked product" as used herein are intended to cover any leavened flour containing product. In addition to bread, the terms include breakfast breads, such as croissants, bagels, "English Muffins" and the like; muffins, pizza crusts, leavened pretzels, leavened cakes, sweet rolls, and so forth. The prewetted psyllium is incorporated into the dough so as to yield a product containing anywhere from about 1.0 to about 5.0 grams of psyllium per ounce of product. Generally, it is preferred that the product contain from about 1.5 to about 3.75 grams of psyllium per ounce of product.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A dough product comprising
    a) at least one flour ingredient,
    b) a leavening agent, and
    c) an amount of prewetted psyllium ranging from about 1.0 to about 5.0 grams per one ounce of said dough product.

2. The dough product of claim 1, further comprising a gluten product.

3. The dough product of claim 1, wherein said flour ingredient is selected from the group consisting of wheat flour, rye flour, and whole wheat flour.

4. The dough product of claim 1, wherein said leavening agent is a yeast.

5. The dough product of claim 1, wherein said dough product is a bread, a muffin, a pizza crust, a pretzel, a sweet roll, a croissant, a bagel, or an English muffin.

6. The dough product of claim 5, wherein said dough product is a bread.

7. The dough product of claim 1, wherein said prewetted psyllium is ground, cold extruded psyllium.

8. Method of making an edible psyllium-enriched dough product comprising:
   a) mixing at least one flour ingredient and water, to form a dough base;
   b) adding prewetted psyllium to said dough base;
   c) adding a leavening agent to said dough base;
   d) mixing said dough base, prewetted psyllium and leavening agent to form a mixture, and;
   e) baking said mixture to form a dough product.

9. The method of claim 8, wherein said flour ingredient is selected from the group consisting of wheat flour, rye flour and whole wheat flour.

10. The method of claim 8, wherein said leavening agent is yeast.

11. The method of claim 8, further comprising adding a gluten to said mixture.

12. Method for reducing serum cholesterol in a subject in need thereof comprising administering to said subject an amount of the dough product of claim 1, sufficient to reduce the serum cholesterol level of said subject.

13. Method for preparing a dough product comprising:
   a. forming an extruded psyllium pellet comprising psyllium, sweetening agent and a flour ingredient;
   b. grinding said extruded psyllium pellet to form a psyllium powder;
   c. prewetting said psyllium powder to form a psyllium composition;
   d. blending said psyllium composition obtained in step c. with a dough base so as to form a dough product and
   e. baking the dough product of step d.

14. Method for claim 13, said extruded psyllium pellet is formed by cold extrusion.

* * * * *